(12) United States Patent
Hanson et al.

(10) Patent No.: US 10,679,756 B1
(45) Date of Patent: *Jun. 9, 2020

(54) HEALTH AND WELLNESS MANAGEMENT TECHNOLOGY

(71) Applicant: Alarm.com Incorporated, Tysons, VA (US)

(72) Inventors: Mark Andrew Hanson, Fairfax, VA (US); Christopher Silverman, Alexandria, VA (US); Adam T. Barth, Annandale, VA (US)

(73) Assignee: Alarm.com Incorporated, Tysons, VA (US)

(*) Notice: Subject to any disclaimer, the term of this patent is extended or adjusted under 35 U.S.C. 154(b) by 571 days.

This patent is subject to a terminal disclaimer.

(21) Appl. No.: 15/357,531

(22) Filed: Nov. 21, 2016

Related U.S. Application Data (63) Continuation of application No. 13/828,596, filed on Mar. 14, 2013, now Pat. No. 9,501,613.

(60) Provisional application No. 61/637,587, filed on Apr. 24, 2012.

(51) Int. Cl.
*G06Q 50/00* (2012.01)
*G06F 17/18* (2006.01)
*G16H 50/50* (2018.01)
*G06N 20/00* (2019.01)

(52) U.S. Cl.
CPC .............. *G16H 50/50* (2018.01); *G06F 17/18* (2013.01); *G06N 20/00* (2019.01)

(58) Field of Classification Search
CPC ...... G05B 19/048; G06N 5/025; G06N 3/008; G06N 5/046; G06N 7/06; H04L 67/12; H04L 12/282; H04L 2012/285; G06K 9/00335; G06K 9/00362; G06K 9/00342; G06K 9/00369; G06K 9/00671; G06K 9/6269; G06Q 30/0261; G06Q 10/06; G06Q 10/087; G06Q 20/203
See application file for complete search history.

(56) References Cited

U.S. PATENT DOCUMENTS

2008/0001735 A1* 1/2008 Tran .................... G06F 19/3418
340/539.22

* cited by examiner

*Primary Examiner* — Maroun P Kanaan
(74) *Attorney, Agent, or Firm* — Fish & Richardson P.C.

(57) ABSTRACT

Health and wellness management technology, in which events that relate to activity within the monitored property are sensed based on output from sensors located at a monitored property. Behaviors are detected based on the sensed events that relate to activity within the monitored property and, in accordance with the detected behaviors, one or more models are created based on a likelihood of similarly expressed events happening at similar times with similar characteristics. Additional behaviors detected after creation of the one or more models are evaluated against the one or more models to determine whether the additional behaviors are consistent with the one or more models. At least one action is performed based on the determination of whether the additional behaviors are consistent with the one or more models.

20 Claims, 8 Drawing Sheets

HEALTH AND WELLNESS MANAGEMENT TECHNOLOGY

CROSS REFERENCE TO RELATED APPLICATIONS

The present application is a continuation of U.S. application Ser. No. 13/828,596, filed Mar. 14, 2013, which claims the benefit of U.S. Provisional Application No. 61/637,587, filed Apr. 24, 2012, each of which are incorporated herein by reference in their entirety for all purposes.

TECHNICAL FIELD

This disclosure relates to health and wellness management technology.

BACKGROUND

Recent advancements in wireless sensing and imaging have facilitated the instrumentation of living environments for a variety of applications spanning from home security to health and wellness monitoring. Such sensing and imaging are contributing to a deluge of data, nearly doubling every five years. Yet the translation of this abundant and esoteric data into instructive information (e.g., health and wellness assessment) remains an elusive product design goal.

In addition to sensing innovations, proliferation of automation (e.g., lights, locks, thermostats, etc.) and mobile devices has realized the vision of a connected home and connected life, responsive to stimuli from the environment or from people interacting in the environment. Such devices offer flexibility of functionality with the promise of anytime, anywhere awareness and control. Yet the optimal configuration and utilization of such devices is still challenging for most consumers.

Management of health and wellness often involves numerous caregiving stakeholders, including the direct user, formal (e.g., clinicians and care professionals) and informal (e.g., family) caregivers, and monitoring professionals. Stakeholders each require different modes of engagement. For example, whereas a direct user may desire hands-on, proactive self-management, a caregiver may only want to know how and when to intervene in response to compromised health or wellness. Furthermore, minimization of false-positives and confirmation of notification are both useful for event-triggered sensing modalities in health and wellness deployments. Therefore, synthesis of sensed phenomena, intelligent decision-making, and user interaction are beneficial to meeting application requirements for sensitivity, selectivity, and safety-criticality. Yet timely, actionable, and appropriate stakeholder engagement, direction, and intervention are not present in state-of-the-art solutions.

SUMMARY

Techniques are described for managing health and wellness.

Implementations of the described techniques may include hardware, a method or process implemented at least partially in hardware, or a computer-readable storage medium encoded with executable instructions that, when executed by a processor, perform operations.

The details of one or more implementations are set forth in the accompanying drawings and the description below. Other features will be apparent from the description and drawings, and from the claims.

DETAILED DESCRIPTION

Techniques are described for managing health and wellness. For example, to facilitate management of health and wellness, artificially intelligent computation is used to transform esoteric sensor data into actionable information. Actions are taken to assist individuals in health and wellness management based on the actionable information derived.

Figure 1:
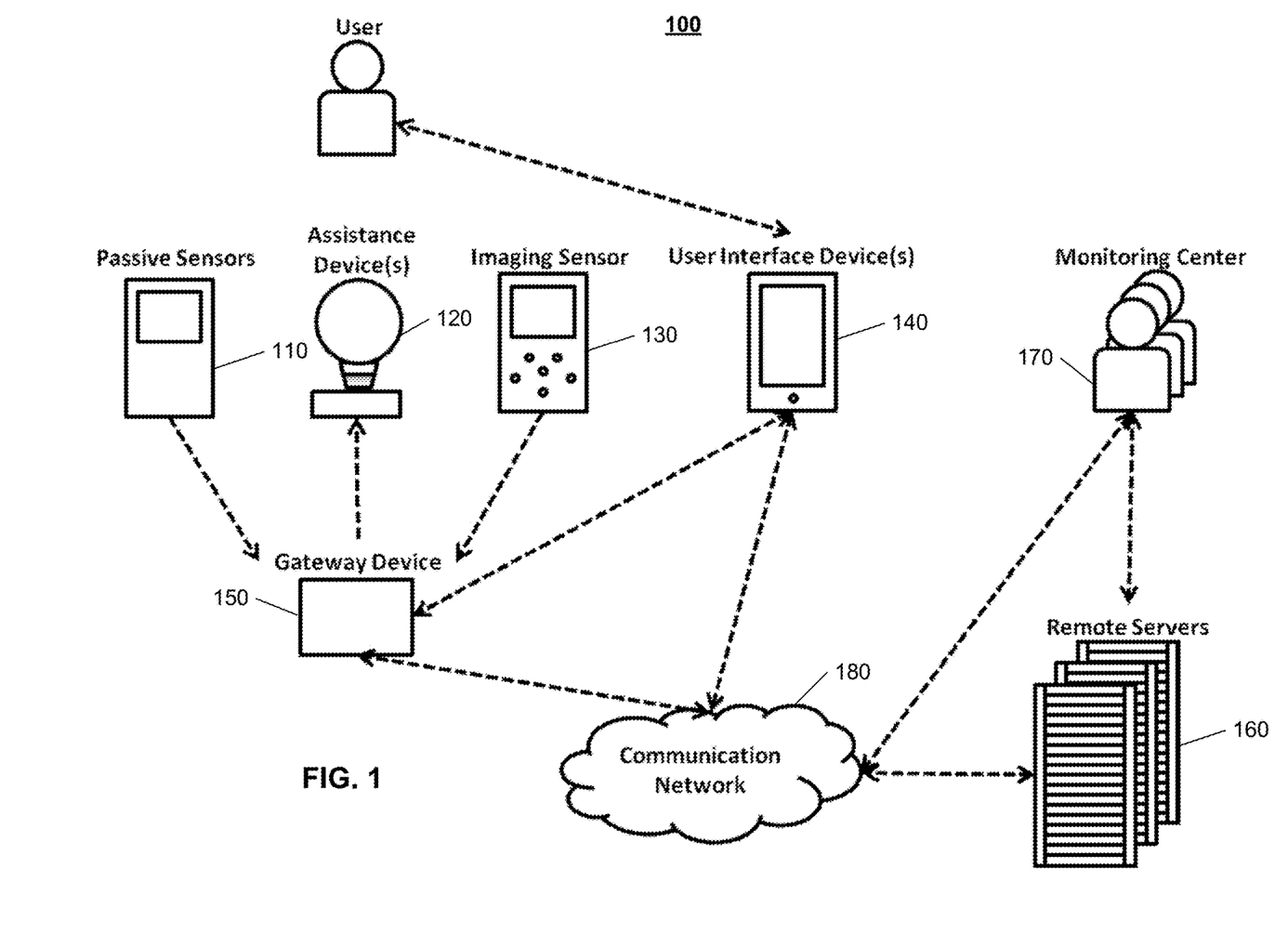
FIGS. 1, 4, and 7 illustrate example systems.

FIG. 1 illustrates an example system 100 configured to manage health and wellness. The system 100 may include one or more passive sensors 110, one or more assistance devices 120, one or more imaging sensors 130, one or more user interface devices 140, a gateway device 150, one or more remote servers 160, and a monitoring center 170. The system 100 may include passive sensors 110, assistance devices 120, and imaging sensors 130, but also may include implementations that do not include one or more of the passive sensors 110, the assistance devices 120, and the imaging sensors 130. The one or more user interface devices 140, the gateway device 150, the one or more remote servers 160, and the monitoring center 170 may exchange communications over a communication network 180.

Passive sensors 110 may be employed to measure activity or inactivity within a monitored residence. The activity or inactivity can be associated with safety compromising events (e.g., wandering, falls, missed medication, etc.) or it can measure aspects of behavior related to health or wellness (e.g., general activity level, sleeping, eating, bathroom use, medication adherence rate, gait speed, etc.).

The passive sensors 110 may include any types of sensors or detectors that are used by monitoring systems (e.g., home security systems) to detect activity. For example, the passive sensors 110 may include a contact sensor (e.g., a door/window contact sensor), a motion sensor (e.g., a PIR motion sensor), a glass break sensor, or any other type of sensor included in an alarm system or security system. The passive sensors 110 also may include an environmental sensor, such as a temperature sensor, a water sensor, a rain sensor, a wind sensor, a light sensor, a smoke detector, a carbon monoxide detector, an air quality sensor, etc. The passive sensors 110 further may include a health monitoring sensor, such as a prescription bottle sensor that monitors taking of prescriptions, a blood pressure sensor, a blood sugar sensor, a bed mat configured to sense presence of liquid (e.g., bodily fluids) on the bed mat, bathroom usage sensors, food consumption sensors, etc. In some examples, the passive sensors 110 may include a radio-frequency identification (RFID) sensor that identifies a particular article that includes a pre-assigned RFID tag.

Assistance devices 120 are capable of performing automated tasks based on inputs from the passive sensors 110, the gateway device 150, the user interface device(s) 140, and/or the remote servers 160. Assistance devices 120 can be programmed to respond based on rules specified by users, by caregivers, monitoring agents, or by default. For example, a light can be illuminated in response to a bed sensor being vacated during the evening. Assistance devices 120 can also report their state to other devices, systems, or stakeholders.

Imaging sensors 130 (e.g., still frame or video) are capable of capturing specific events or recording one or more images proximal in time or location to specific events (e.g., entering or leaving home). Furthermore, imaging sensors 130 paired with identity recognition routines can be utilized to identify an individual associated with specific events (e.g., specific person entering or leaving home). Imaging sensors 130 may also have other modes of sensing (e.g., motion, acceleration, etc.) to trigger or augment native imaging and sensing capabilities.

A user interface device 140 can be used to communicate information to or gather information from a user about health, wellness, safety, or general activity. Possible physical incarnations of user interface devices 140 may include light or audio sources, displays, push buttons, and mobile devices (e.g., mobile phones or mobile phone applications). The user interface devices 140 may include a web interface, a web browser, or any device that operates an application that communicates over a network, such as the Internet.

A user interface device 140 may also act as a sensing device and relay data to the gateway device 150 or directly to the remote servers 160 through the communication network 180. For example, the user interface device 140 may actively seek a response from a user (e.g., via push button) to confirm a detection of an activity or passively monitor activity with one or more built-in sensors. User interface devices 140 can also prompt the user to perform activities conducive to health and wellness. A user interface device 140 may also be given to caregivers or care management professionals outside of the monitored residence. For example, a homecare worker could use a user interface device 140 to check-in to a monitored residence or annotate user records.

The gateway device 150 can be used to relay information between remote servers 160 (e.g., over a public or private communication network) and systems at the user location. The gateway device 150 can also allow systems proximal to a user's location to communicate without involvement from the remote servers 160. Certain incarnations of the system 100 may not include a gateway device 150. Therefore, the passive sensors 110, the assistance devices 120, or the user interface devices 140 may be connected directly to the communication network 180.

The remote servers 160 may be employed to store, process, and initiate actions based upon health and wellness events, or other data collected about each monitored user and location. The remote servers 160 may also capture or accept data from other data sources, such as from other remote servers or devices connected via communication network 180. For example, data may be captured or accepted from electronic medical records to provide additional context for artificially intelligent processes. Monitoring center agents can also annotate user records stored on the remote servers 160.

A monitoring center 170 may employ automated or human agents to observe user events and contact users or caregivers based on defined protocols, quantitative or qualitative assessments. Monitoring center agents can also annotate records stored on the remote servers 160 about a user.

Figure 2:
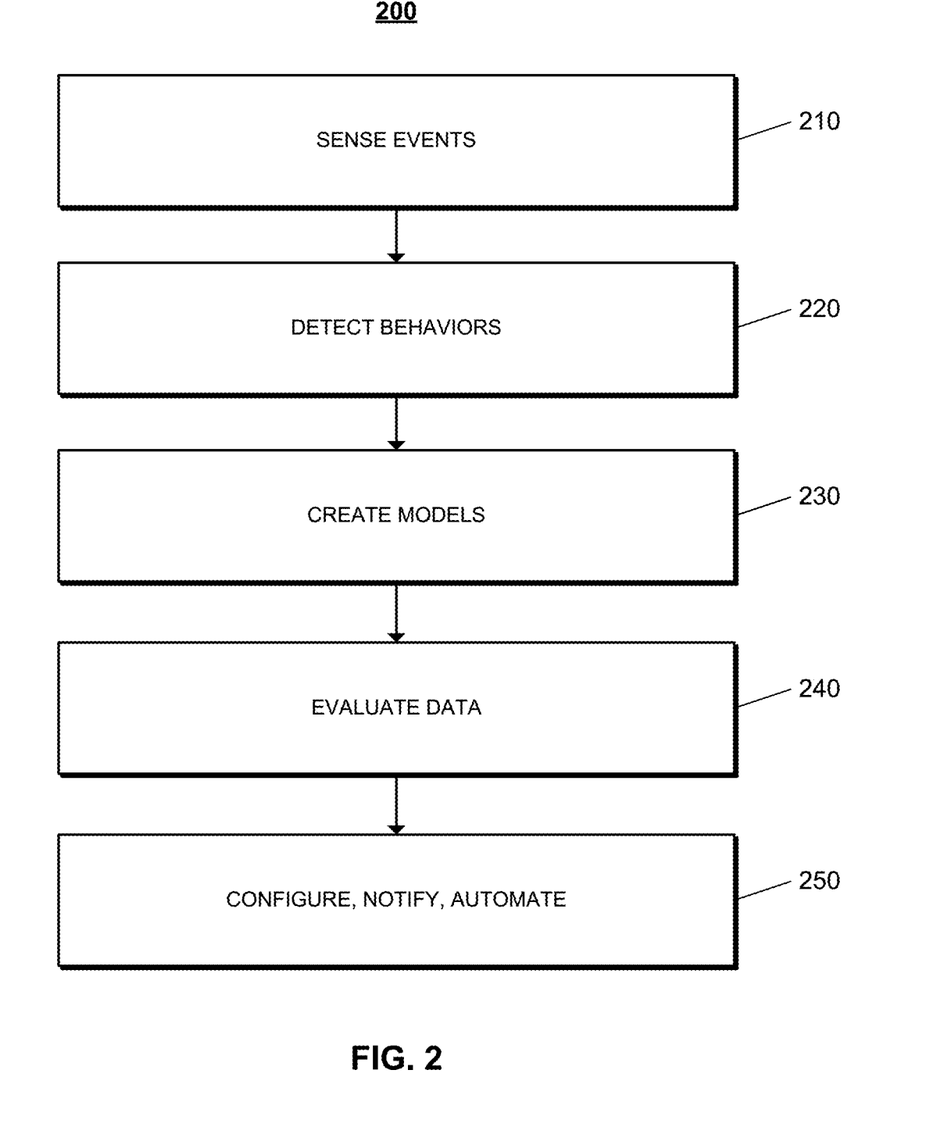
FIG. 2 is a flow chart illustrating an example process.

FIG. 2 illustrates an example process 200 for health and wellness management. The operations of the example process 200 are described generally as being performed by the system 100. The operations of the example process 200 may be performed by one of the components of the system 100 or may be performed by any combination of the components of the system 100. In some implementations, operations of the example process 200 may be performed by one or more processors included in one or more electronic devices.

To facilitate management of health and wellness, artificially intelligent computation is used to transform esoteric sensor data into actionable information. For instance, the health and wellness management process 200 includes event sensing (210), behavior detection (220), model creation (230), data evaluation (240), and configuration, notification, and/or automation actions (250). The operations of the process 200 are independent; however, the operations work together when staged sequentially to assist users in system configuration and analysis of data. Although the process 200 is described as having a multiplicity of steps, a subset of steps can be employed to still meet practical requirements of information processing and analysis in this application domain.

The system 100 senses events (210). For example, the system 100 senses events that relate to activity within the monitored property using any of the sensors described throughout this disclosure. In this example, the system 100 may sense events using data captured by the passive sensors 110, the imaging sensors 130, and/or the user interface devices 140.

In some examples, the system 100 performs sensor synthesis in sensing events. Sensor synthesis refers to the process by which multiple physical sensor data streams are grouped into a synthesized data stream. The synthesis provides mechanisms for fine-grained temporal gating and windowing, as well as an explicit process to define data aggregation behavior. Sensor synthesis can occur at a physical point of data aggregation (e.g., on sensor or at gateway device) or entirely on remote servers. Any partitioning of logic between computational platforms may be used.

Figure 3:
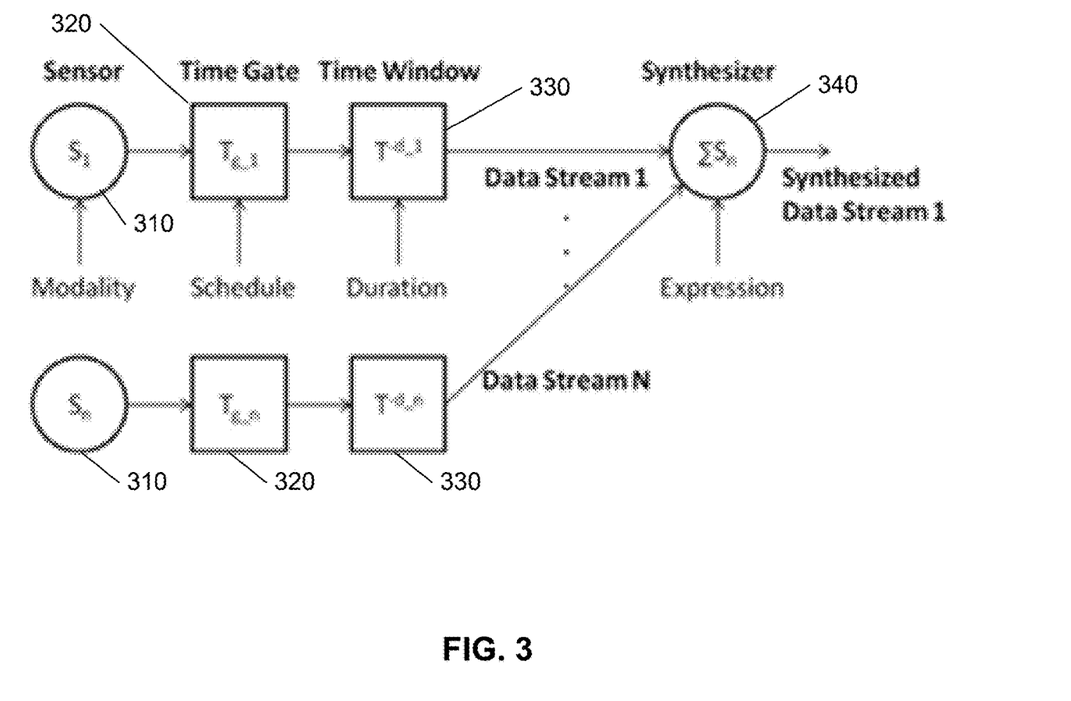
FIG. 3 illustrates example sensor synthesis.

FIG. 3 illustrates example sensor synthesis that may be performed by the system 100. First, for each stream, the modality of the raw sensor data stream is configured (310). Sensors are capable of outputting normal data or data that satisfies an exception rule. For example, a door or window contact sensor can output both "close" and "open" events (e.g., normal data) or only "open" events (e.g., exception data). Modality selection may reduce accumulated data, increasing system efficiency for latter stage processing and archiving.

Second, for each stream, the sensor data stream is time-gated (320). An explicitly-defined schedule may be created to set coarse boundaries when sensor data is valid. For example, a motion sensor data stream could pass data for evening hours only. Therefore, during the day, no data would be forwarded through the time gate. As with setting the sensor modality, time gating may increase system efficiency by focusing system intelligence on exceptional events.

Third, for each stream, the sensor data stream is time-windowed (330). An explicitly-defined duration may set temporal boundaries between the present time and a past time for which sensor data is treated as a whole. For example, the system 100 may analyze the quantity of door open events within the past five minutes (e.g., duration). This sliding window enables fine-grained temporal assessment, which may increase situational awareness.

Fourth, multiple sensor data streams are aggregated using a synthesizer (340). For example, the synthesizer defines the stream aggregation behavior using an explicit stream logic expression. The stream logic represents a method by which streams may be defined programmatically. The logic treats streams as objects and allows for arithmetic and logical operations via metadata expressions. Expressions are interpreted and executed in software operating on hardware devices or by hardware alone. A precise syntax need not be used and any suitable syntax may be used. Below, a simple example is shown:

---
Stream Algebra Logic Example:
---
outstream = instream(1) + instream(2) + instream(3);
---

In some implementations, the synthesizer aggregates multiple sensor data streams without stream logic. However, the stream logic may offer increased functionality and flexibility.

The synthesized data stream enables higher-level data association. For example, the synthesizer could average the reported temperature of a thermostat over a day, average motion-triggered events across numerous PIR motion sensors, or even apply a digital filter to a single or multiple data streams. Although sensor stream logic is described above, sensor selection and aggregation behavior also may be defined without the use of such metadata or expressions.

Referring again to FIG. 2, the system 100 detects behaviors (220). For instance, the system 300 translates individual sensor streams or synthesized streams into human behaviors (e.g., activities of daily living).

Through a heuristic classification (e.g., expert system approach), sensor stream data is translated into behaviors which are representative of or approximations of activities of daily living (e.g., sleeping, eating, general activity, etc.). The translation is based on a multiplicity of specified variables including, but not limited to: Current sensor state, Change in sensor state, Duration in sensor state, Time of day, Type of sensor, Location of sensor, Identity of Individual Triggering Sensor, and Stream States, which are the states at the output of stream algebra. For example, a door sensor placed on a cabinet or refrigerator could be used to detect activity in a kitchen. For specific activations lasting a period of time, the data may be interpreted as meal preparation and food consumption. Definitions of behaviors may be explicitly specified within classification processes or through explicitly defined stream logic as illustrated above.

In some implementations, confidence of activity classification can be assigned based on heuristics or from a priori multivariate analysis. For example, an "eating event" classification confidence score may be assigned if a kitchen motion sensor is activated for a period of time. If a refrigerator is also opened, the confidence may increase based on the higher degree of correlation between refrigerator events and eating.

The system 100 creates one or more models (230). The system 100 may create behavior or stream models based on the likelihood of similarly expressed events or streams happening at similar times or with similar characteristics. For example, stream or behavior events or states may be stored longitudinally on remote servers and the stored behaviors or streams may be profiled to create stochastic models of activity. Behaviors and activity may be modeled based on any or all of the following parameters: Quantity, Occurrences or Lack of Occurrences, Duration, Time, Location, Sequences of Behaviors, Individual Exhibiting Behaviors, Individual Medical or Other Records, and User Feedback or Training Data.

Furthermore, modeling may be performed based on combined streams or behaviors. For example, activity in the bathroom resulting from a combination of sensors (e.g., motion, bathroom occupancy, etc.) may be analyzed by a clustering process (example below) to find contiguous periods of a behavior and determine likelihood of the behavior occurring during the bounds specified by the process. Such clustering may also result in Gaussian mixture model approximations of activity.

A multiplicity of models may be created to suit a variety of profiling needs (e.g., days of the week, time of the year, visitors to the residence, or medication cycles). Individual models may be aggregated to form larger population-based models of behavior across residences, demographics, institutions, specific conditions, etc.

Example of Clustering Process

---
Example of Clustering Process:
---
1) Define Maximum Cluster Count
2) Define Minimum Cluster Weight
3) Define Starting Standard Deviation Threshold
4) Calculate Time Between Adjacent Events
5) Calculate Mean and Standard Deviation of Distances
6) Create Ordered List of Distances, Event Tuples
7) Select Smallest Distance to Create First Cluster
8) Iterate Through Ordered List of Tuples to Create Aggregate Clusters If Distance Between Cluster's Boundary Event and New Event Is Less than Standard Deviation Threshold
9) Prune Clusters of Insufficient Cluster Weight or Clusters Within Existing Cluster Bounds
10) Expand Standard Deviation Threshold If Actual Cluster Count Exceeds Maximum Cluster Count
---

The system 100 evaluates collected data (240). For instance, the system 100 evaluates recently detected behaviors against the created models to determine whether the recently detected behaviors are consistent with the models or suggest a change that may indicate a problem. The system 100 also may evaluate past behavior data and created models to identify behavioral trends that may be problematic.

In some examples, data may be evaluated against statistical parameters of single-user historic data, multi-user historic data, or even against explicitly-set thresholds. The data may include both synthesized data streams as well as archived user data. Therefore, evaluation may occur in real-time or after a period of time. Furthermore, evaluation may be made against unprocessed incoming data, or against statistically evaluated incoming data.

Figure 4:
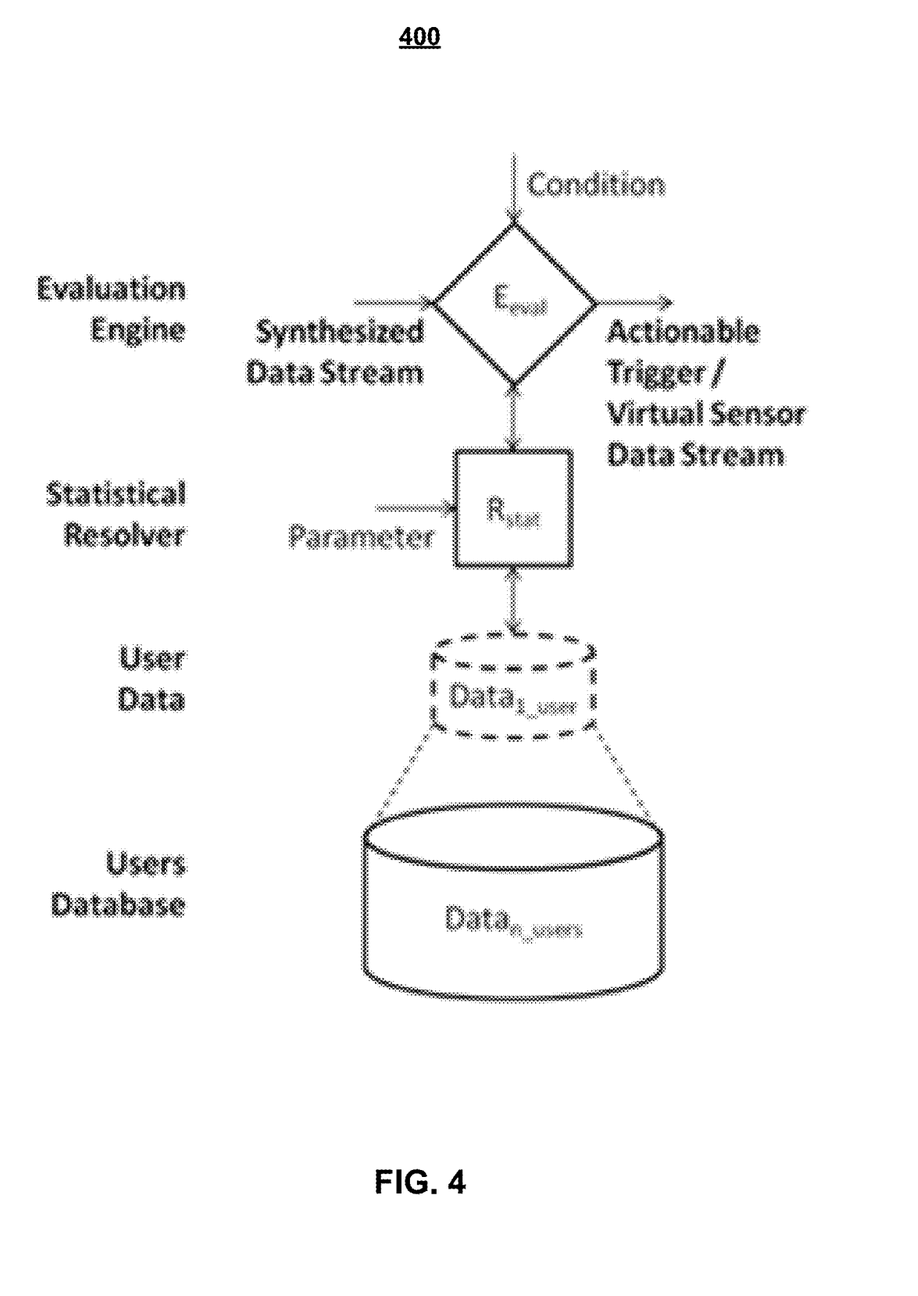

FIG. 4 illustrates an example evaluation system 400. The evaluation system 400 may be included in the system 100. As shown, an evaluation engine is capable of executing conditional statements and producing a virtual sensor output. A virtual sensor is a processed output that may be used to trigger other actions, or act as a sensor itself. The virtual sensor may generate a real-time or delayed output. Therefore, either synthesized stream data or historic data may be compared against mined database statistics or an explicitly set condition (e.g., threshold). The virtual sensor data stream may become the input to another level of sensor synthesis (e.g., nested virtual sensing forms complex, yet modular logic). Alternatively, the output may be used as an actionable trigger (e.g., Boolean evaluation to dispatch a notification or automation procedure). Logical conditions include, but are not limited to: less than, greater than, equal to, less than or equal to, greater than or equal to, not equal to, in range, and out of range.

A statistical resolver resides between the evaluation engine and a system-wide user database. The resolver may compute statistical parameters including, but not limited to: mean, median, mode, variance, and standard deviation. The parameters may be computed for the user's incoming data, the user's historic data, or from the historic data of all users. Steps for behavior or stream evaluation are discussed in more detail below.

The system 400 compares behaviors or streams to corresponding behavior or stream models (e.g., either individual or population). These comparisons may include behavior correlation or deviation from expected norms.

The system 400 measures the results of comparisons against rules or thresholds created for applications related to the behaviors or stream in question. Population norms may be utilized to augment behavior models or help inform threshold selection.

The system 400 scores behavior or stream events scored on a spectrum of routine to atypical based on comparison to their model. The scoring may be based on deviation of the event from the model.

The system 400 analyzes behavior or stream events or their classifications on longer time scales to elucidate trends. Such trends may be informative of more subtle changes in lifestyle, wellbeing, or health. These trends also may be utilized to alert of or elicit behavior change.

Referring again to FIG. 2, the system 100 performs configuration, notification, and/or automation actions (250). For instance, actions may be taken based on behavior models, trend analysis, or classification results. The actions may include any type of action desired. For example, system settings may be recommended or automatically configured based on normative behavior models or population augmented data. Alerts may be generated from classification results and sent to the resident, caregivers, or a remote monitoring center. Actions such as home automation of lights, locks, thermostat settings, etc. may be initiated due to specific rules related to behaviors. Direct resident feedback may be obtained from user interface devices such as mobile phones to measure the accuracy of processed data. Information may be synthesized for diagnostic purposes and subsequently fed back to users to elicit behavior change. Professional caregivers may initiate or prioritize contact or a visit with one or more users based on scored health or wellness metrics.

Figure 5:
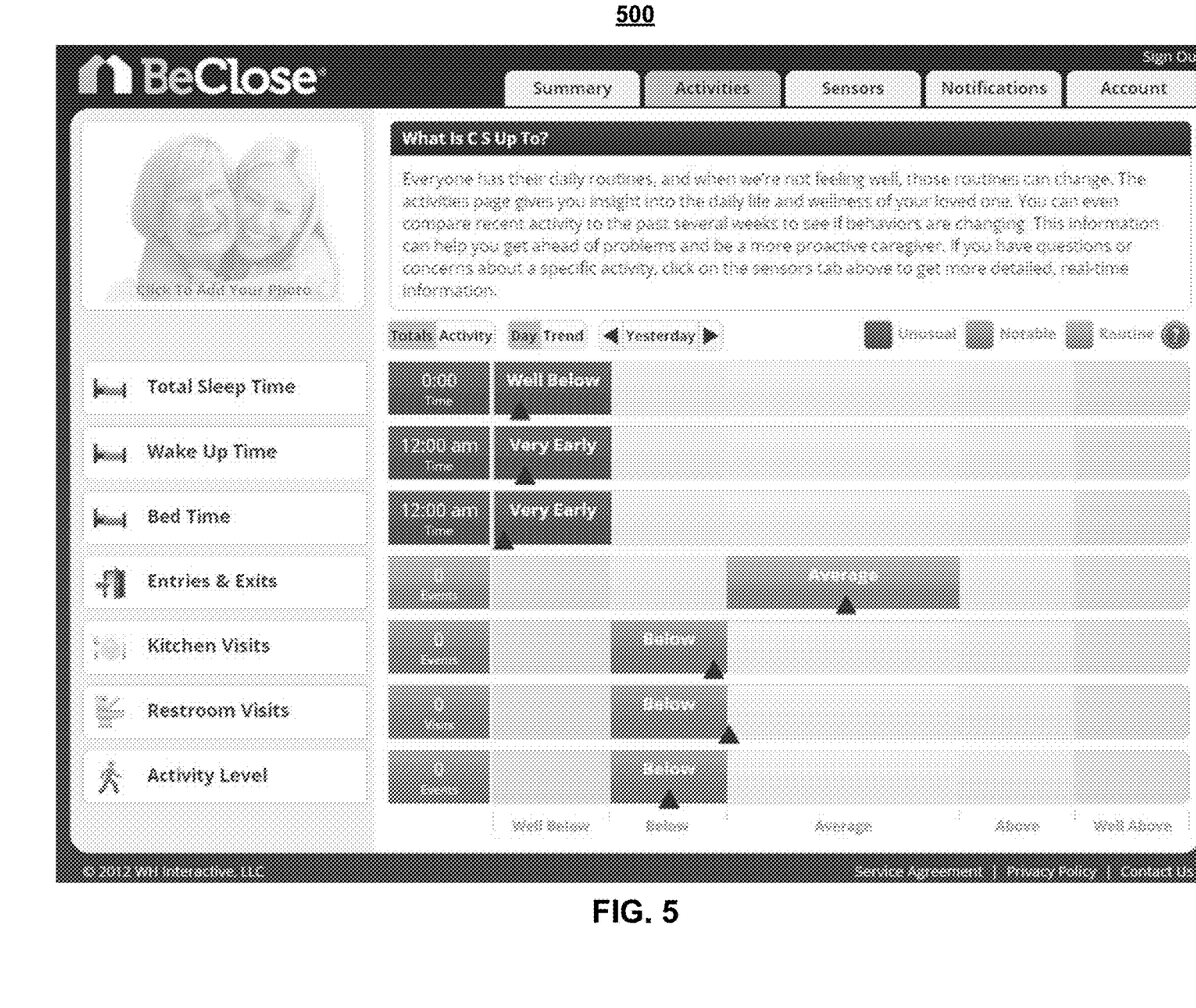
FIGS. 5 and 6 illustrate example user interfaces.
Figure 6:
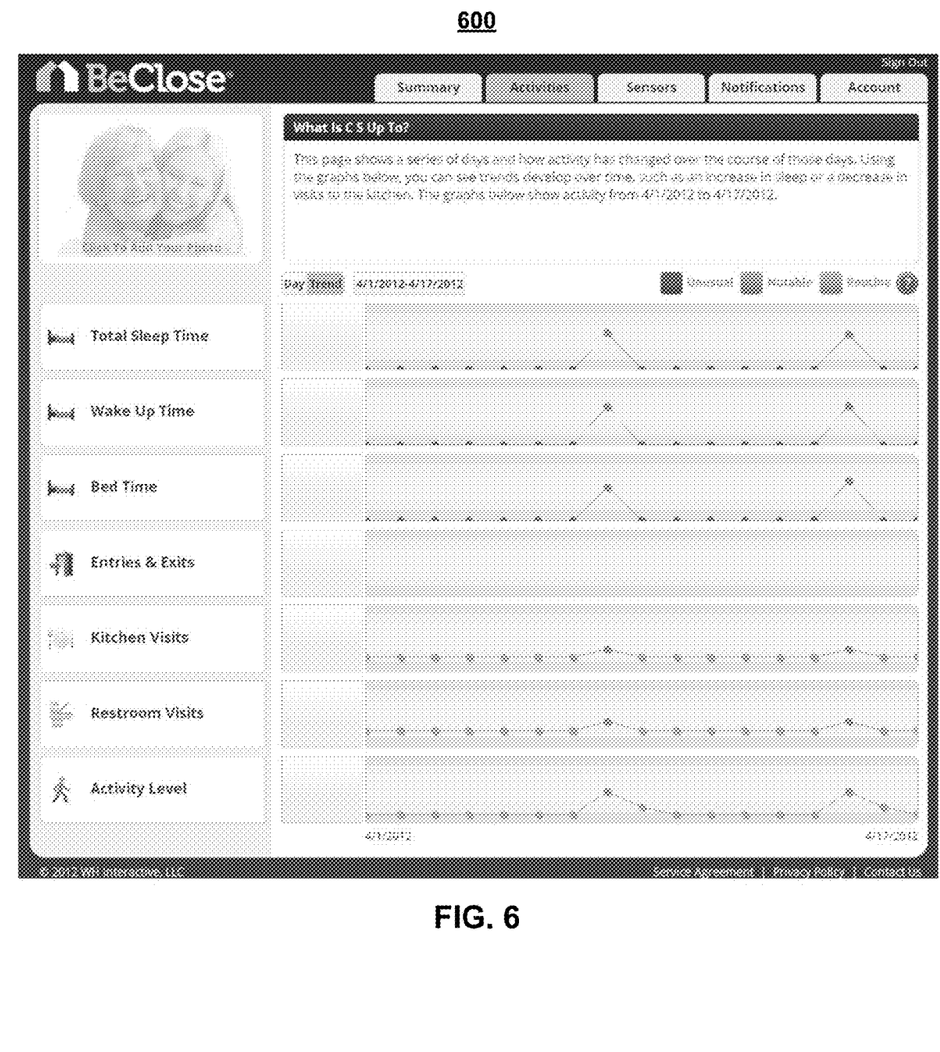

FIGS. 5 and 6 illustrate example reports that the system 100 may provide. As shown in FIG. 5, a report 500 illustrates a classification of aggregate behavior events. For each behavior, the report 500 provides a graphical indication of whether the detected activity (e.g., events) related to the behavior is well-below average, below average, average, above average, or well above average. As shown, the detected activity (e.g., events) related to entries and exits is shown to be below average, the detected activity (e.g., events) related to kitchen visits is shown to be average, and the detected activity (e.g., events) related to general activity level is shown to be average.

In FIG. 6, a report 600 illustrates trend analysis of aggregated behavior events. For each behavior, the report 600 provides a graphical indication of whether the detected activity (e.g., events) related to the behavior is well-below average, below average, average, above average, or well above average for each day over a user-selectable window, which is set to a one week long period of time.

From system generated actions, the system 100 may measure outcomes to help tune intervention, therapy, or behavior change based on continuous measurement. For example, if few meals are detected through the course of measurement, the system 100 may generate reminders or notifications to eat more. If, following notification, meal patterns remain unchanged, the system 100 may follow-up with corrective action or initiate notification.

Figure 7:
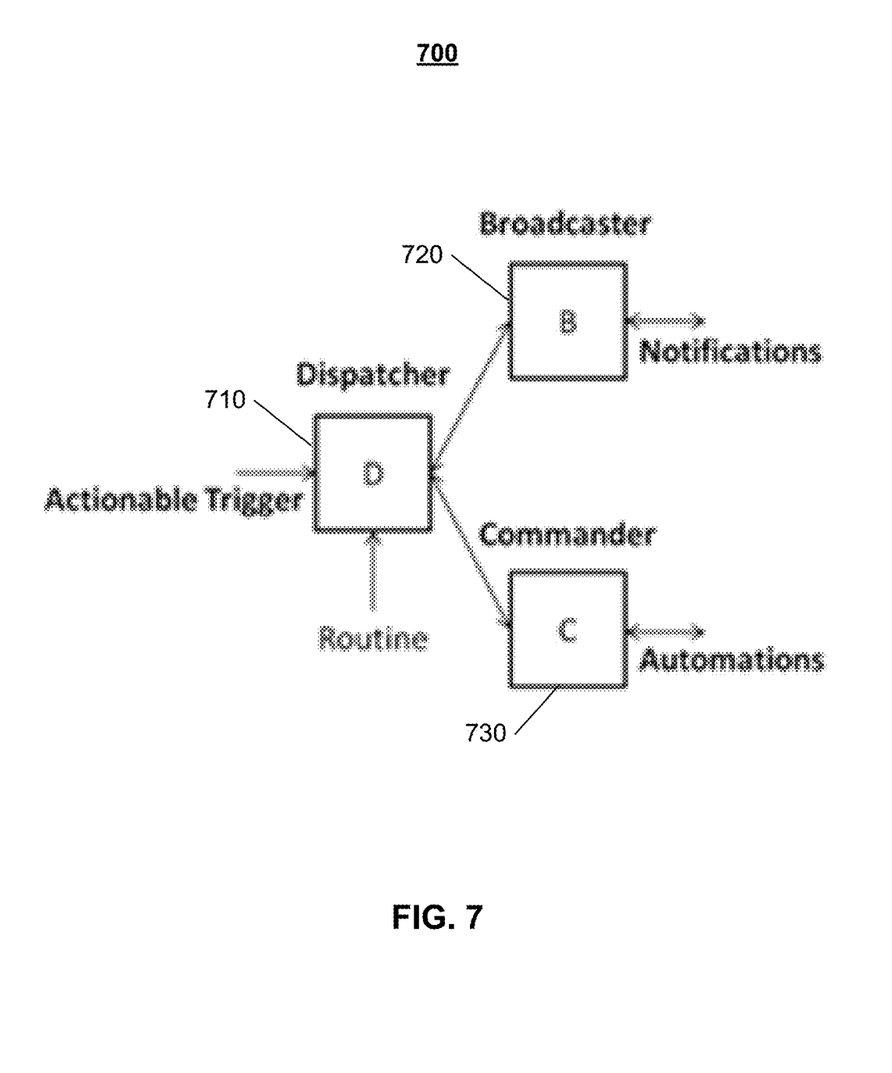

FIG. 7 illustrates an example automated dispatcher-based system 700 that may achieve interactive action. The system 700 may be included in the system 100 and may be used in performing configuration, notification, and/or automation actions (250). The system 700 provides an ability to flexibly schedule notification, automation, or intervention procedures, request confirmation of action, and prompt new actions when confirmations are not received or when previous actions have completed. Additionally, the system 700 may support rich interactivity, which encompasses an ability, by both users and caregivers, to annotate events.

The system 700 may include a dispatcher 710, a broadcaster 720, and a commander 730. The dispatcher 710, the broadcaster 720, and the commander 730 can be connected and exchange electronic communications to coordinate configuration, notification, and automation actions. The dispatcher 710, the broadcaster 720, and the commander 730 may be embodied as separate modules within a single electronic device or may be embodied in separate electronic devices.

In performing configuration, notification, and automation actions, the dispatcher 710 can receive an actionable trigger. The dispatcher 710 is programmed with an explicitly-defined routine. The routine includes a prioritized schedule of notification, automation, and intervention procedures. The schedule can be arranged as a binary decision tree, in the example shown below, the procedures are rendered in a table format. As depicted, actions may be scheduled in response to triggers or in response to receipt of confirmed notifications, automation or intervention procedures. In Table 1 shown below, if an action trigger is generated (e.g., Action Trigger=1), then two notifications are immediately generated (e.g., to Contact 1 and Contact 2). If no notification receipt is received in a pre-defined timeout period, then a message is forwarded to a call center. Such a structure creates an opportunity for flexible notification dispatching. In this example, both serialized and parallel responses are possible, ensuring that events are acted upon reliably and in a timely manner.

TABLE 1

Example Action Routine

| State | Action | Condition 1 | State 1 | Condition 2 | State 2 |
|---|---|---|---|---|---|
| 1 | Wait | Action Trigger = 1 | 2 | Action Trigger = 0 | 1 |
| 2 | Call Contact 1 | True | 3 | N/A | N/A |
| 3 | Call Contact 2 | Notification Receipt | 1 | Notification Timeout | 4 |
| 4 | Forward Central Station | Notification Receipt | 1 | Notification Timeout | 4 |

Items in the schedule are dispatched to either the broadcaster 720 (e.g., for notifications) or the commander 730 (e.g., for automations). The broadcaster 720 attempts to notify the desired party, by a prescribed communication medium (e.g., telephone, e-mail, SMS/MMS, Facebook or Twitter feed, etc.), all as specified within the routine. The broadcaster 720 attempts to deliver and elicit a response from the contacted party, creating a receipt to confirm delivery of a notification. The commander 730 attempts to perform an automation task by sending commands to any registered control device (e.g., thermostat, lock, light, etc.). The commander 730 reports the status of the sent automation command (e.g., success, failure). As previously noted, responses may be subsumed in the action routine.

Annotations may be attached to events for reporting purposes and to syndicate rich, interactive content for a single user or across groups of users in the system 700. For example, a user may acknowledge receipt of notification and enter a descriptive text string to communicate and clarify information pertaining to the event (e.g., at the user interface device). The responses/annotations also may be used to train machine learning mechanisms for automated detection of anomalous events.

The dispatcher 710 also may be used to effectively manage the utilization of caregiving professionals. For example, based on a health or wellness assessment, an action trigger may be generated to notify a formal caregiver to visit a user. Receipt of the visit may be logged from a professional caregiver's user interface device (e.g., GPS check-in), and annotations may be entered for the monitored resident.

Through a combination of synthesized sensing, intelligent evaluation, and interactive actions, sophisticated sensor-automation-notification behaviors may be created. User interfaces providing access to sensor modality, time-gate schedule, time window duration, synthesis expression, evaluation expressions, and action routines, remove the need for system-wide reprogramming if new capabilities are needed. Moreover, system presets (e.g., created organizationally and organically by users themselves) accommodate widely-used intelligent, interactive behaviors (e.g., Up-and-About, Sensor-Light Interaction, etc.).

Because the systems described herein are flexible, the systems may be trained to learn proper responses to observed phenomena. For example, a user's annotations and responses could be applied to validate the detection of events and further train the system 100 to elicit desired actions (e.g., supervised learning).

Figure 8:
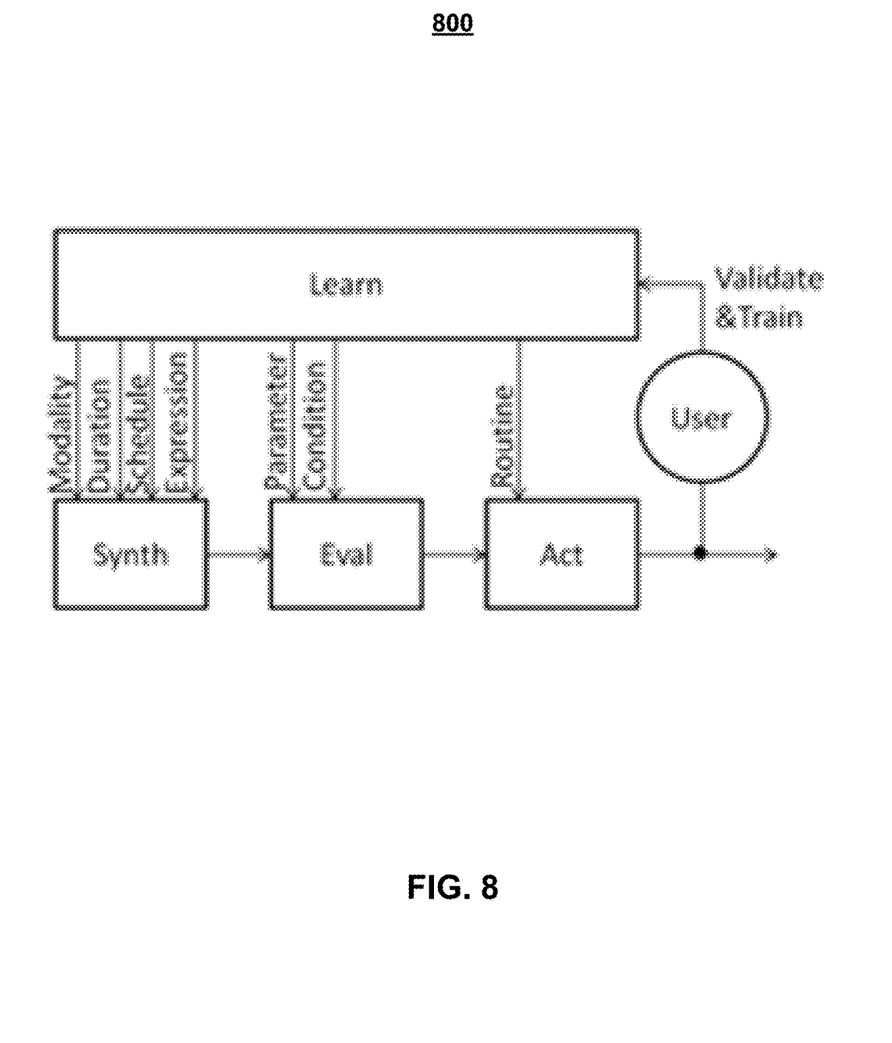
FIG. 8 is a diagram illustrating an example learning mechanism.

FIG. 8 illustrates an example learning mechanism 800. The learning mechanism 800 may be included in the system 100. The learning mechanism 800 may control the system synthesis, evaluation, and action stages to increase system efficiency and effectiveness. The learning and control mechanism may take one of many forms, including but not limited to: artificial neural network, genetic process, fuzzy control, expert system, etc. The use of machine learning provides human-assisted feedback control for health and wellness management.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially-designed ASICs (application-specific integrated circuits).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

What is claimed is:

1. A method comprising:
   receiving, by a monitoring server, data from sensors located throughout a monitored property;
   configuring multiple sensor streams that each correspond to a particular sensor of the sensors located throughout the monitored property;
   aggregating the multiple sensor streams into a synthesized data stream for a particular user of a plurality of users;
   creating one or more models based on identified human behaviors within the synthesized data stream and multiple synthesized data streams that include the synthesized data stream, wherein each of the multiple synthesized data streams corresponds to a distinct user of the plurality of users;
   after creating the one or more models, detecting a subsequent behavior;
   based on detection of the subsequent behavior, comparing the one or more created models with the subsequent behavior at least by analyzing parameters that represent the detected subsequent behavior against statistical parameters obtained from one or more of the multiple synthesized data streams;
   determining, based on the comparison between the one or more created models and the subsequent behavior, that the subsequent behavior is inconsistent with human behaviors modeled by at least one of the one or more created models;
   initiating a home automation action based on determining that the subsequent behavior is inconsistent with the human behaviors modeled by the at least one of the one or more created models;
   performing the home automation action by at least one device within the monitored property; and
   sending a notification of the performed home automation action to a user associated with the monitored property.

2. The method of claim 1 further comprising:
   scheduling a home automation action based on a prioritized schedule of automation;
   sending an instruction to perform the home automation action based on the timing of the prioritized schedule of automation; and
   reporting a status of the home automation action.

3. The method of claim 1 wherein performing the home automation action by at least one device within the monitored property comprises performing the home automation by at least one of a light, a lock, or a thermostat.

4. The method of claim 1 wherein identifying human behaviors within the synthesized data stream comprises:
translating the synthesized data stream into approximations of daily human behaviors using heuristic classification.

5. The method of claim 1 wherein identifying human behaviors within the synthesized data stream comprises:
translating the synthesized data stream into approximations of daily human behaviors using a stream logic algebraic expression.

6. The method of claim 1 wherein creating one or more models based on identified human behaviors within the synthesized data stream comprises:
storing behavior events longitudinally on the monitoring server that is remote from the monitored property, wherein a portion of the stored behavior events are based on the one or more synthesized data streams that are synthesized from prior streams of sensor data aggregated for distinct users of the plurality of users; and
profiling the stored behavior events to create stochastic models of activity.

7. The method of claim 1 wherein creating one or more models based on identified human behaviors within the synthesized data stream comprises:
modeling behaviors and activity based on quantity, occurrences, lack of occurrences, duration, time, location, sequences of behaviors, individual exhibiting behaviors, individual medical records, and user feedback.

8. The method of claim 1 wherein creating one or more models based on identified human behaviors within the synthesized data stream comprises:
analyzing activity sensed from a combination of sensors using a clustering process to find contiguous periods of a particular behavior and determine likelihood of the particular behavior occurring during bounds specified by the clustering process.

9. The method of claim 1 further comprising:
evaluating past behavior data and the one or more created models to identify behavioral trends that are identified as problematic.

10. The method of claim 9 wherein evaluating past behavior data and the one or more created models to identify behavioral trends that are identified as problematic comprises evaluating the past behavior data and the one or more created models against statistical parameters of single-user historic data, multi-user historic data, or set thresholds.

11. The method of claim 9 wherein the evaluated data includes the synthesized data streams and archived user data.

12. The method of claim 1 wherein sending a notification of the performed home automation action to a user associated with the monitored property comprises sending a notification to at least one of a resident of the monitored property, a caregiver associated with the monitored property, and a remote monitoring center associated with the monitored property.

13. The method of claim 1 wherein reporting a status of the home automation action comprises providing a graphical indication of the subsequent behavior.

14. A system comprising:
at least one processor; and
at least one memory coupled to the at least one processor having stored thereon instructions which, when executed by the at least one processor, causes the at least one processor to perform operations comprising:
receiving, by a monitoring server, data from sensors located throughout a monitored property;
configuring multiple sensor streams that each correspond to a particular sensor of the sensors located throughout the monitored property;
aggregating the multiple sensor streams into a synthesized data stream for a particular user of a plurality of users;
creating one or more models based on identified human behaviors within the synthesized data stream and multiple synthesized data streams that include the synthesized data stream, wherein each of the multiple synthesized data streams corresponds to a distinct user of the plurality of users;
after creating the one or more models, detecting a subsequent behavior;
based on detection of the subsequent behavior, comparing the one or more created models with the subsequent behavior at least by analyzing parameters that represent the detected subsequent behavior against statistical parameters obtained from one or more of the multiple synthesized data streams;
determining, based on the comparison between the one or more created models and the subsequent behavior, that the subsequent behavior is inconsistent with human behaviors modeled by at least one of the one or more created models;
initiating a home automation action based on determining that the subsequent behavior is inconsistent with the human behaviors modeled by the at least one of the one or more created models;
performing the home automation action by at least one device within the monitored property; and
sending a notification of the performed home automation action to a user associated with the monitored property.

15. The system of claim 14 wherein performing the home automation action by at least one device within the monitored property comprises performing the home automation by at least one of a light, a lock, or a thermostat.

16. The system of claim 14 further comprising:
evaluating past behavior data and the one or more created models to identify behavioral trends that are identified as problematic.

17. The system of claim 16 wherein evaluating past behavior data and the one or more created models to identify behavioral trends that are identified as problematic comprises evaluating the past behavior data and the one or more created models against statistical parameters of single-user historic data, multi-user historic data, or set thresholds.

18. The system of claim 16 wherein the evaluated data includes the synthesized data streams and archived user data.

19. The system of claim 14 wherein sending a notification of the performed home automation action to a user associated with the monitored property comprises sending a notification to at least one of a resident of the monitored property, a caregiver associated with the monitored property, and a remote monitoring center associated with the monitored property.

20. At least one computer-readable storage medium encoded with executable instructions that, when executed by at least one processor, cause the at least one processor to perform operations comprising:
receiving, by a monitoring server, data from sensors located throughout a monitored property;

configuring multiple sensor streams that each correspond to a particular sensor of the sensors located throughout the monitored property;

aggregating the multiple sensor streams into a synthesized data stream for a particular user of a plurality of users;

creating one or more models based on identified human behaviors within the synthesized data stream and multiple synthesized data streams that include the synthesized data stream, wherein each of the multiple synthesized data streams corresponds to a distinct user of the plurality of users;

after creating the one or more models, detecting a subsequent behavior;

based on detection of the subsequent behavior, comparing the one or more created models with the subsequent behavior at least by analyzing parameters that represent the detected subsequent behavior against statistical parameters obtained from one or more of the multiple synthesized data streams;

determining, based on the comparison between the one or more created models and the subsequent behavior, that the subsequent behavior is inconsistent with human behaviors modeled by at least one of the one or more created models;

initiating a home automation action based on determining that the subsequent behavior is inconsistent with the human behaviors modeled by the at least one of the one or more created models;

performing the home automation action by at least one device within the monitored property; and sending a notification of the performed home automation action to a user associated with the monitored property.

* * * * *